United States Patent [19]

Larock et al.

[11] Patent Number: 4,868,304

[45] Date of Patent: Sep. 19, 1989

[54] SYNTHESIS OF NITROGEN HETEROCYCLES

[75] Inventors: Richard C. Larock, Ames, Iowa; Srinivasan Babu, Maryland Heights, Mo.

[73] Assignee: Iowa State University Research Foundation, Inc., Ames, Iowa

[21] Appl. No.: 200,716

[22] Filed: May 27, 1988

[51] Int. Cl.$^4$ .................. C07D 217/24; C07D 215/22
[52] U.S. Cl. .................... 546/141; 546/139; 546/149; 546/153; 546/157; 546/166; 546/181; 548/486; 548/508
[58] Field of Search .............. 546/141, 139, 149, 153, 546/157, 166, 181; 548/486, 508

[56] References Cited

U.S. PATENT DOCUMENTS

| | | | |
|---|---|---|---|
| 3,331,846 | 7/1967 | Easton et al. | 546/153 |
| 3,428,644 | 2/1969 | Aeberli et al. | 548/486 |
| 3,939,164 | 2/1976 | Kaiser et al. | 546/139 |
| 4,200,754 | 4/1980 | Holden et al. | 546/141 |

OTHER PUBLICATIONS

Chemical Abst., vol. No. 87, Entry No. 84760c, 1977.
Chemical Abst., vol. No. 88, Entry No. 169998j, 1978.
Chemical Abst., vol. No. 88, Entry No. 169999k, 1978.
Chemical Abst., vol. No. 91, Entry No. 175155k, 1979.
Chemical Abst., vol. No. 91, Entry No. 140635q, 1979.
Chemical Abst., vol. No. 92, Entry No. 76062s, 1980.
Chemical Abst., vol. No. 93, Entry No. 71411r, 1980.
Chemical Abst., vol. No. 95, Entry No. 115293b, 1981.
Chemical Abst., vol. No. 96, Entry No. 68395v, 1982.
Chemical Abst., vol. No. 96, Entry No. 122554m, 1982.
Chemical Abst., vol. No. 96, Entry No. 181087j, 1982.
Chemical Abst., vol. No. 99, Entry No. 175611w, 1983.
Chemical Abst., vol. No. 99, Entry No. 175613y, 1983.
Chemical Abst., vol. No. 100, Entry No. 102553h, 1984.
Chemical Abst., vol. No. 100, Entry No. 138984p, 1984.
Chemical Abst., vol. No. 101, Entry No. 171049f, 1984.
Chemical Abst., vol. No. 102, Entry No. 45857a, 1985.
Chemical Abst., vol. No. 104, Entry No. 19471s, 1986.
Chemical Abst., vol. No. 106, Entry No. 102016j, 1987.

*Primary Examiner*—Glennon H. Hollrah
*Assistant Examiner*—James H. Turnipseed
*Attorney, Agent, or Firm*—Zarley, McKee, Thomte, Voorhees & Sease

[57] ABSTRACT

A method of synthesizing nitrogen heterocycles such as indoles, indolines, oxindoles, quinolines, isoquinolines, and isoquinolones, all of which are pharmacologically active. The method involves cyclizing a haloaryl alkene in the presence of a catalytically effective amount of a palladium(II) ion source and in the presence of a cyclizing promoting base such as an alkali metal salt.

12 Claims, No Drawings

SYNTHESIS OF NITROGEN HETEROCYCLES

BACKGROUND OF THE INVENTION

Chemical methods of synthesizing indoles, indolines, oxindoles, quinolines, isoquinolines, and isoquinolones are known. However, all such reactions generally operate only under heroic conditios and as well provide the desired heterocyclic product in low yields.

These above-referred-to compounds are extremely important compounds for a variety of reasons. For example, because of the very potent and diverse biological activity exhibited by indole and its various derivatives, this heterocyclic system has been the target of considerable attention in chemistry, biology and medicine. Indole derivatives are essential to both plants and animals. Skatole [3-methylindole], which can be isolated from various sources, is reported to have antidiuretic and tuberculostatic activity. Tryptophan, a naturally occurring amino acid is known to inhibit the growth of tuberculosis. Indole acetic acid is a major plant growth horomone and indomethacin has been reported to have antiinflammatory, antipyretic and analgesic activity.

Quinolines, too, are important. A number of quinoline alkaloids have been isolated from rutaceous plants. Among them as edulitine, folimine and folifidene. These alkaloids and many others bearing the quinoline ring systems possess important biological properties and have been the target of synthesis for many years. Though many synthetic approaches have been described, none are satisfactory for high yield, economic production.

Much interest in the isoquinoline alkaloids has also developed over the years and several new naturally occurring compounds have been found. Plants belonding to the fmaily Cactaceae are known to contain simple tetrahydroisoquinolines. Naturally occurring doryanine and doryfomine were isolated from sassafras tree. A number of isoquinoline alkaloids possessing important biological properties exist in nature and many of them have been synthesized in the laboratory.

In short, it can be seen that there is a real and continuing need for a convenient synthesis for the classes of compounds referred to herein. Many are useful as being derived from natural products, others are synthetically derived, but all are known to have physiological properties and exhibit a wide variety of pharmacological activity.

It is a primary objective of the present invention to prepare nitrogen heterocycles by palladium catalyzed intramolecular cyclization of haloaryl alkenes to provide in high yield compounds such as indoles, indolines, oxindoles, quinolines, isoquinolines, and isoquinolones.

SUMMARY OF THE INVENTION

A method of synthesizing compounds such as indoles, indolines, oxindoles, quinolines, isoquinolines and isoquinolones by intramolecular cyclization of haloaryl alkenes in the presence of palladium(II) and a cyclization promotion-effective base such as an alkali metal salt, like sodium acetate.

DETAILED DESCRIPTION OF THE INVENTION

An illustrative reaction of the present invention can be demonstrated by the following intramolecular cyclization reaction equation:

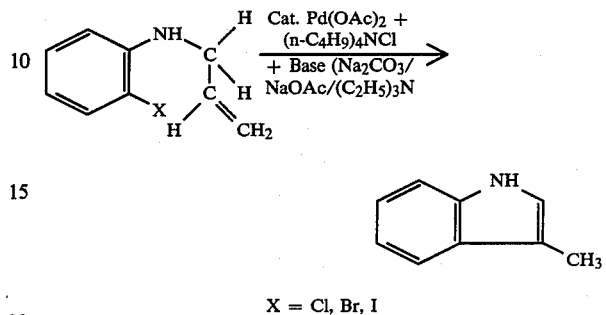

X = Cl, Br, I

In this reaction it can be seen that an ortho-haloaryl alkene is cyclized, that is intramolecularly condensed, to provide an indole. In the reaction, X represents a halide moiety and it can be chloride, bromide or iodide. Iodides are preferred.

The intramolecular condensation or cyclization equation that is here illustrated is shown to prepare an indole, but it is understood that it is within the scope of this invention to prepare by a completely analogous reaction not only indoles but also indolines, oxindoles, quinolines, isoquinolines and isoquinolones. Each of these is illustrated in the examples below.

In order to make the reaction go, the reaction must be promoted by a catalytic amount of a palladium(II) ion or a palladium(O) reagent such as tetrakis-(triphenylphosphine)Palladium(O). The precise source of the palladium(II) ion when used is not critical. Most preferably the salt is a palladium(II) water soluble salt and is palladium acetate. However, it may also be conducted in the presence of palladium chloride and other palladium water soluble salts as well. The amount of palladium present is an amount sufficient to effectively promote the intramolecular cyclization on a catalytic basis. Generally, the amount should be within the range of about 0.5 mole percent of the initial reactants up to about 5 mole percent of the initial reactants, with a preferred amount being from about 1.5 to 3.0 mole percent.

In order to promote the reaction, it is necessary that the reaction be conducted in the presence of a cyclization promoting effective amount of a base. Suitable bases may be selected from alkali metal salts of weak acids such as sodium carbonate and sodium acetate, or they may be organic bases such as triethylamine. The amount of the base added may vary from 1.0 equivalents up to 3.0 equivalents in comparison with the amount of the haloaryl alkene. Generally it has been found preferable to use a molar excess, and 2.5 equivalents of the base in comparison with the haloaryl alkene provides the most satisfactory results.

It has been found that the yields are significantly increased if the reaction is run in the presence of a yieldenhancing organic solvent. The most preferred solvent is dimethylformamide (DMF). Other simple polar solvents may be used as well, such as tetrahydrofuran, methyl alcohol, diethyl ether, hexamethylphosphoramide, acetonitrile and the like.

The temperature at which the reaction is run is not critical, indeed it is one of the advantages of the invention that it can be run at room temperature. Generally speaking, temperatures are from 0° C. up to 150° C. can be used. Likewise, the reaction does not appear to be time dependant and satisfactory results can range from about 0.5 hours up to 72 hours, with the typical reaction going to completion within 12 hours or less.

All three bases, that is triethylamine, sodium acetate and sodium carbonate are effective for preparation of each of indoles, indolines, oxindoles, quinolines, isoquinolines, and isoquinolones.

The following examples are offered to illustrate, but not limit, the process of this invention.

EXAMPLES

In the examples 1-12 of this invention, as shown in the Table below, the following reaction conditions were used. All reactions were stirred in a culture tube at the table designated temperature using 2% palladium acetate (0.005 mmol), an appropriate base (0.625 mmol), the haloaryl alkene (0.25 mmol), the solvent dimethylformamide (0.4 ml), and n-Bu$_4$NCl (0.25 mmol), unless otherwise specified. All products gave appropriate $^1$H and $^{13}$C NMR, IR, and mass spectral or combustion analysis data. One equivalent of NaO$_2$CH was also added in the synthesis of indolines (see Example 5 in the Table).

TABLE I

Synthesis of Nitrogen Heterocycles[a]

| Example | Substrate | Base (2.5 equiv) | Reaction Time (days) | Temp. (°C.) | Heterocycle[b] | Isolated Yield (%) |
|---|---|---|---|---|---|---|
| 1 | R = H | Na$_2$CO$_3$ | 1 | 25 | | 97 |
| 2 | R = CH$_3$ | Et$_3$N | 2 | 25 | | 81 |
| 3 | R = COCH$_3$ | NaOAc | 1 | 80 | | 90 |
| 4 | | Et$_3$N | 1 | 80 | | 73 |
| 5 | | Et$_3$N | 1 | 80 | | 65[c] |
| 6 | | NaOAc | 1 | 80 | | 97 (84[d]) |
| 7 | | Na$_2$CO$_3$ | 1 | 25 | | 92-97 |
| 8 | | NaOAc | 1 | 80 | | 55 |

TABLE I-continued

Synthesis of Nitrogen Heterocycles[a]

| Example | Substrate | Base (2.5 equiv) | Reaction Time (days) | Temp. (°C.) | Heterocycle[b] | Isolated Yield (%) |
|---|---|---|---|---|---|---|
| 9 | (2-iodobenzyl)(allyl)amine | Na$_2$CO$_3$ | 1 | 80 | 4-methylisoquinoline | 39 |
| 10 | (2-iodobenzyl)amine with cinnamoyl | NaOAc | 1 | 100 | 2-benzylidene-1-(2-aminobenzyl) ketone | 39[e,f] |
| 11 | 2-iodo-N-allylbenzamide | Et$_3$H | 1 | 100 | 1-hydroxy-4-methylisoquinoline | 58[e] |
| 12 | 2-iodo-N-(4-phenyl-3-butenyl)benzamide | Na$_2$CO$_3$ | 1 | 110 | 3-benzylidene-isoquinolin-1(2H)-one | 33[f] |

[a]All reactions were stirred in a culture tube at the appropriate temperature using 2% Pd(OAc)$_2$ (0.005 mmol), an appropriate base (0.625 mmol), the substrate (0.25 mmol), DMF (0.4 ml) and n-Bu$_4$NCl (0.25 mmol) unless otherwise specified.
[b]All products gave appropriate $^1$H and $^{13}$C NMR, IR, and mass spectral or combustion analysis data.
[c]One equivalent of NaO$_2$CH was added.
[d]Recrystallized yield; E/Z mixture as determined by $^{13}$C NMR.
[e]Pd(PPh$_3$)$_4$ was used instead of Pd(OAc)$_2$.
[f]Product as observed by $^{13}$C NMR consists of one isomer of undetermined stereochemistry.

As illustrated in the examples, these reactions are preferably conducted in the presence of tetra-n-butylammonium chloride, generally one equivalent. This is not essential, but preferred both for increased rate of reaction and increased yield. Other tetralkylammonium salts or tetralkylphosphonium halide salts may be used as well.

As can be seen in the Table, each of the bases prove equally effective. Substitution on the nitrogen slowed the reaction, but good yields of indoles could still be obtained by allowing the reaction to proceed longer at room temperature (Example 2) or running the reaction at 80° C. (Example 3). Substitution on the double bond also slowed the reaction, but a high yield of indole could still be obtained (Example 4).

Oxindoles were readily available by this reaction (Example 6) and can be prepared in a near quantitative yield.

It therefore can be seen that the catalyst system in the present invention in the presence of an appropriate base is an excellent catalyst system for the cyclization of a variety of nitrogen-containing haloaryl alkenes. The alkene portion of the starting moiety is not limiting, but generally it is a C$_3$ to C$_{20}$ alkene moiety with a nitrogen moiety and other substituents as desired, for example, alkyl substitutions, alkoxy substitutions, keto substitutions, carbonyl substitutions or the like. All the reactions reported in Examples 1-12 proceeded under milder conditions than those previously reported in the literature, provide higher yields than similar reactions reported in the literature, and/or involve the synthesis of heterocycles that were not previously known to be capable of preparation by palladium catalyzed cyclization. It therefore can be seen that the invention acccomplishes at least all of its stated objectives.

What is claimed is:

1. A method of synthesis of nitrogen heterocycles by catalyzed intramolecular cyclization, comprising: cyclizing a haloaryl alkene to provide a nitrogen heterocycle in high yield, said cyclization occurring in the presence of a catalytically effective amount of a palladium source and in the presence of a cyclization promoting effective amount of a base.

2. The process of claim 1 wherein said halo group is selected from the group of chloride, bromide and iodide.

3. The process of claim 1 wherein said halo is iodide.

4. The process of claim 1 wherein said nitrogen heterocycles are selected from the group consisting of indoles, indolines, oxindoles, quinolines, isoquinolines and isoquinolones.

5. The process of claim 1 wherein said haloaryl nitrogen-containing alkene is a C$_3$ to C$_{20}$ alkene.

6. The process of claim 5 wherein said alkene is a C$_3$ to C$_{10}$ alkene.

7. The process of claim 1 wherein said base is selected from the group consisting of alkali metal salts of weak acids and triethylamine.

8. The process of claim 7 wherein said base is sodium carbonate.

9. The process of claim 1 wherein said cyclizing occurs in the presence of a reaction yield-enhancing organic solvent.

10. The process of claim 9 wherein said solvent is dimethylformamide.

11. The method of claim 10 wherein said reaction occurs in the presence of tetra-n-butylammonium chloride.

12. The process of claim 11 wherein said cyclization occurs at a temperature of 20° C. to 80° C. for from 0.5 hours to 72.0 hours. hours.

* * * * *